(12) United States Patent
Endsley et al.

(10) Patent No.: US 9,566,172 B2
(45) Date of Patent: Feb. 14, 2017

(54) METHOD AND APPARATUS FOR DETERMINING A LOCATION

(71) Applicant: Biomet Manufacturing, LLC, Warsaw, IN (US)

(72) Inventors: Jason M. Endsley, Warsaw, IN (US); Mark Mottram, Penshurst (AU); Peter Anthony Brydon, Moorooduc (AU)

(73) Assignee: Biomet Manufacturing, LLC., Warsaw, IN (US)

( * ) Notice: Subject to any disclaimer, the term of this patent is extended or adjusted under 35 U.S.C. 154(b) by 430 days.

(21) Appl. No.: 14/204,831

(22) Filed: Mar. 11, 2014

(65) Prior Publication Data

US 2014/0276866 A1    Sep. 18, 2014

Related U.S. Application Data

(60) Provisional application No. 61/783,697, filed on Mar. 14, 2013.

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61B 17/15* | (2006.01) |
| *A61F 2/36* | (2006.01) |

(52) U.S. Cl.
CPC .............. *A61F 2/4657* (2013.01); *A61B 17/15* (2013.01); *A61F 2/36* (2013.01); *A61F 2002/3611* (2013.01); *A61F 2002/4658* (2013.01)

(58) Field of Classification Search
CPC combination set(s) only.
See application file for complete search history.

(56) References Cited

U.S. PATENT DOCUMENTS

| | | | |
|---|---|---|---|
| 5,578,037 A | 11/1996 | Sanders et al. | |
| 5,728,128 A | 3/1998 | Crickenberger et al. | |
| 5,792,143 A | 8/1998 | Samuelson et al. | |
| 5,860,969 A | 1/1999 | White et al. | |
| 6,258,097 B1 * | 7/2001 | Cook .................... | A61F 2/4657 606/102 |
| 7,022,141 B2 | 4/2006 | Dwyer et al. | |
| 7,695,474 B2 | 4/2010 | Crofford | |
| 7,854,737 B2 | 12/2010 | Daniels et al. | |
| 2009/0076507 A1 | 3/2009 | Claypool et al. | |

* cited by examiner

*Primary Examiner* — Sameh Boles
(74) *Attorney, Agent, or Firm* — Schwegman Lundberg & Woessner, P.A.

(57) ABSTRACT

A template operable to reestablish the center of rotation of a native femoral head at the head of an implanted prosthesis. The template includes a first member with a marking passage and optional cutting guide and a second member with a target. The first member of the template can be placed on a femur and the second member can be moved in the proximal-distal, medial-lateral and anterior-posterior directions to fix the center of the target at the center of rotation of a femoral head. The head of a prosthesis can be manipulated to come in contact with the target to reestablish the center of rotation of the native femoral head.

6 Claims, 8 Drawing Sheets

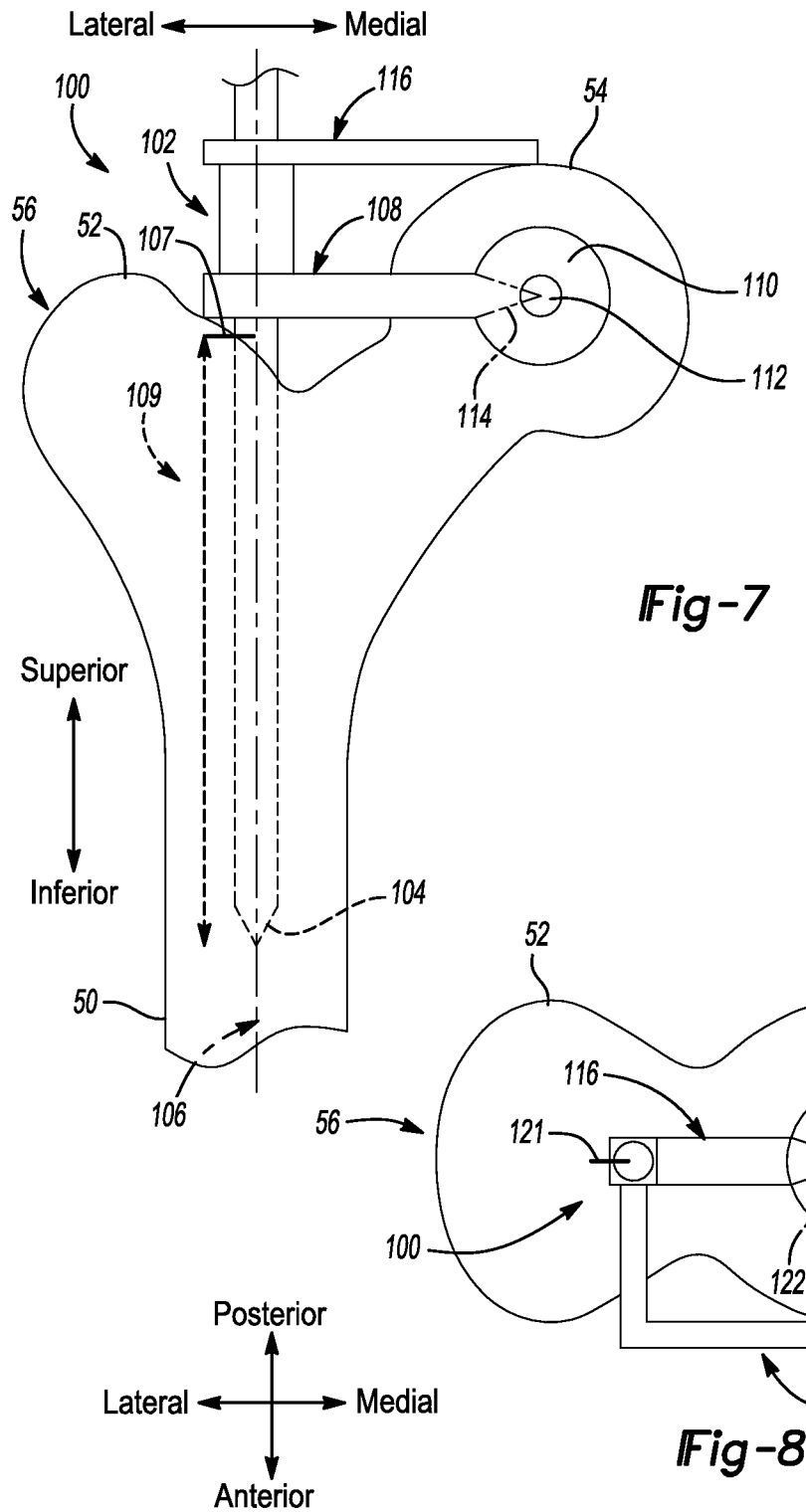

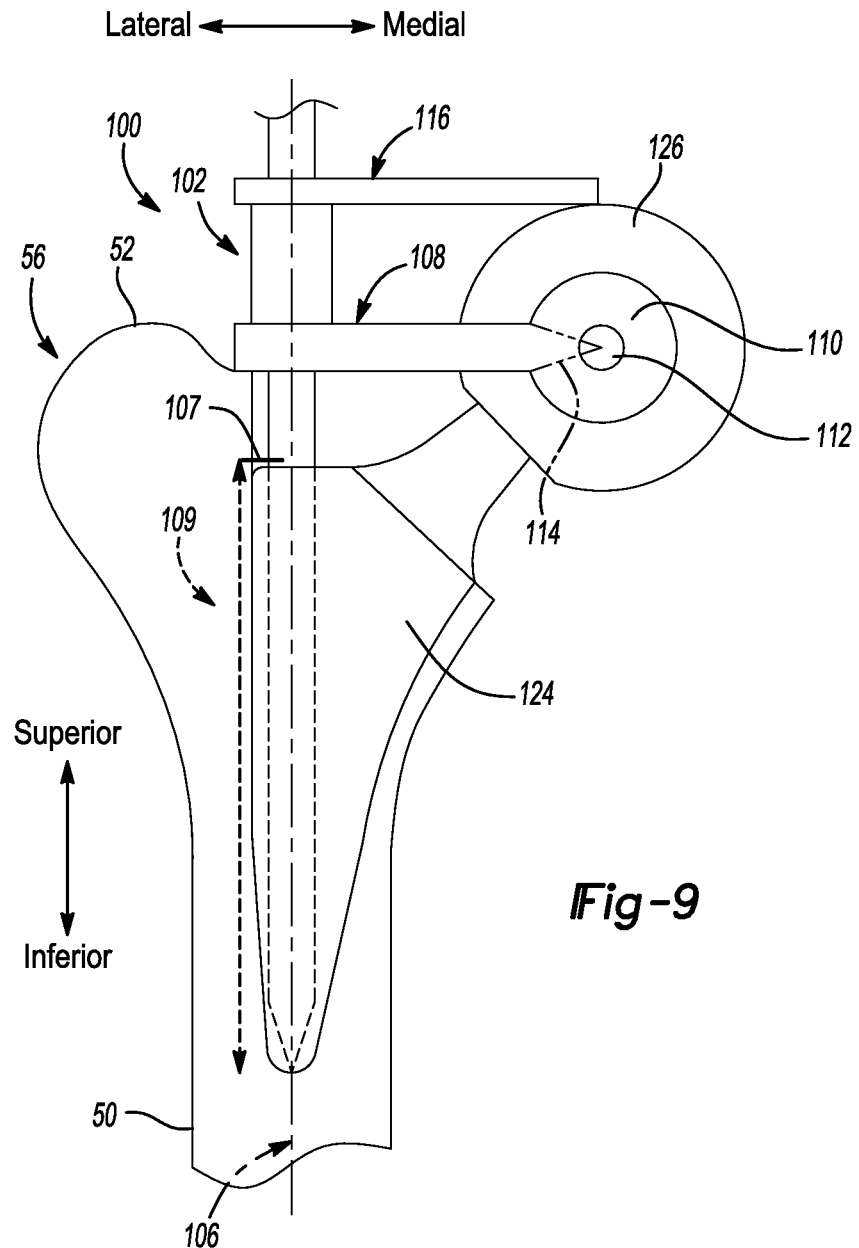

METHOD AND APPARATUS FOR DETERMINING A LOCATION

CROSS-REFERENCE TO RELATED APPLICATIONS

This application claims the benefit of U.S. Provisional Application No. 61/783,697, filed on Mar. 14, 2013. The entire disclosure of the above application is incorporated herein by reference.

FIELD

The present disclosure relates to implant templates for replicating a center of a femoral head.

BACKGROUND

This section provides background information related to the present disclosure which is not necessarily prior art.

During reconstruction of a hip, it is often desirable to reestablish a native head center of a femur with an implanted prosthesis. During a medical procedure, the native head of a femur is often resected early in the procedure, which makes it difficult to position a head center of the prosthesis at the same location and orientation as the native head center of the femur. Generally, a trial prosthesis can be used to approximate or test establishment of a head center during a procedure.

SUMMARY

This section provides a general summary of the disclosure, and is not a comprehensive disclosure of its full scope or all of its features.

The present teachings provide for a device operable as a template operable to locate a head center of a femur. The head center is understood to be the portion of the femoral head that defines a center of rotation of the femoral head when inserted in a natural acetabulum. The head center can be a geometric center of a natural femoral head. The template can include a first member that is held or fixed relative to the greater trochanter, the shaft of the femur, or both. The first member includes a marking feature such as a protrusion or a noncircular-shaped, such as a cross, marking passage by which the femur is marked. The first member can also include a cut guide, which can be used to mark a line or guide an instrument to resect the head of a femur. A second member of the template includes a locator or target to identify the native head center of the femur. The second member is operably connected to the first member so that the target can be moved in a superior-to-inferior, a medial-to-lateral and an anterior-to-posterior direction relative to the anatomy and the fixed first member. One or more locking members can fixedly interconnect the first member and the second member or lock the second member in place relative to the first member, or both. Measurement markings can be incorporated with the first and second members such as where they interconnect, including at or near the locking members, to allow for the reestablishment of desired orientations of the second member relative to the first member.

According to various embodiments, the device for locating the head center of a femur includes a first member configured to be positioned adjacent to at least one of a medial or lateral side of at least one of a shaft of a femur or a greater trochanter of the femur. The first member may contact the anterior or posterior side of the shaft. The first member comprises a marking feature, such as a protrusion or a noncircular passage, to mark the position of the device on the shaft of the femur or on the greater trochanter of the femur. The first member can also include a protractor. A second member of the device extends from the first member. The second member is moveable and fixable relative to the first member. The device also comprises a third member that extends from the second member and is moveable and fixable relative to the first member. The third member includes a target portion configured to be positioned at a head center of a femur while the first member is positioned adjacent to at least one of the medial or lateral side of at least one of the shaft of the femur or the great trochanter of the femur. Further, the device includes a first locking member operable to fix the second member in two planes relative to the anatomy and to the first member and a second locking member to fix the third member relative to the anatomy and to the first member in a third plane. Measurement markings can be incorporated where the first and second members interconnect and where the second and third members interconnect to allow for the reestablishment of desired orientations of the second member relative to the first member.

In yet another embodiment, the device for locating the head center of a femur includes a first member configured to be at least partially inserted into a shaft of a femur. An inferior portion of the first member can be inserted into a shaft of a femur, a broach or a prosthesis, and a superior portion of the first member can remain exterior to the femur. A second member of the device extends from a posterior portion of the first member. The second member is moveable and fixable relative to the first member, and includes a first target portion. The second member can be moved in a first direction relative to the first member to center the first target portion at a first native head center of a femur. A third member of the device extends from the posterior portion of the first member. The third member is moveable and fixable relative to the first member, and includes a second target portion. The third member can be moved in a second direction relative to the first member to center the second target portion at a second native head center of a femur. Additionally, a first locking member can fixedly interconnect the first member and the second member or lock the second member in place relative to the first member, or both. A second locking member can fixedly interconnect the first member and the third member or lock the third member in place relative to the first member, or both.

The present teachings further provide a method for determining a head center of a femur and reestablishing the head center with the head center of an implanted prosthesis during a procedure. The method can include placing a template comprising a first member that is operably connected to a second member by one or more locking members through a surgical opening and positioning the template on an anterior or posterior surface of a femur comprising a shaft and a native head with a center of rotation, wherein the second member includes a target portion configured to be positioned at a native head center of a femur. The method can also include marking the position of the template on the femur by placing a mark on the femur around a marking protrusion on the first member of the template or through a noncircular-shaped marking passage in the first member of the template. The method can also include centering the target portion of the second member at the native head center of the femur by moving the second member in a superior-to inferior, a medial-to-lateral and an anterior-to-posterior direction and either fixing the second member in place relative to the anatomy and the first member by tightening the one or more locking members, using the measurement markings to establish the position of the second member relative to the first member, or both. The method further includes removing the template, resecting the native femoral head, and implanting a prosthesis comprising a head portion into the shaft of the femur. Placing the template at the previous position on the surface of the femur by realigning the mark placed on the femur with the marking protrusion or through the noncircular-shaped marking passage in the first member of the template can allow for the reestablishment of the native head center of the femur by moving the prosthesis so that the head center of the prosthesis comes into contact with the target portion of the template.

According to various embodiments, the method for determining a head center of a femur and reestablishing the head center with a head center of an implanted prosthesis during a procedure includes positioning a template comprising a first member, a second member, and a third member into a shaft of a femur. The femur has a native head with a center of rotation, and the second and third members of the template include target portions configured to be positioned to identify the center of the native femoral head. The method includes centering the target portion of the second and third members near the native head center of the femur by moving the second and third members relative to the first member. When the target portions of the second and third members are directed over the native head center in two directions, the second member and third member are fixed by tightening a first locking member and a second locking member, respectively. When the second and third members are locked into place relative to the first member, the template can be removed from the femur and the native femoral head can be resected. The method further includes inserting a broach or a prosthesis into the shaft of the femur and reestablishing the native head center of the femur by repositioning the template relative to the broach or the prosthesis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7 is a side view of a template positioned within a femur according to the present teachings;

FIG. 8 is a perspective view of the template and femur of FIG. 8; and

FIG. 9 is a side view of the template according to FIG. 5 positioned within a broach or prosthesis inserted into a femur.

Corresponding reference numerals indicate corresponding parts throughout the several views of the drawings.

DETAILED DESCRIPTION

Figure 1:
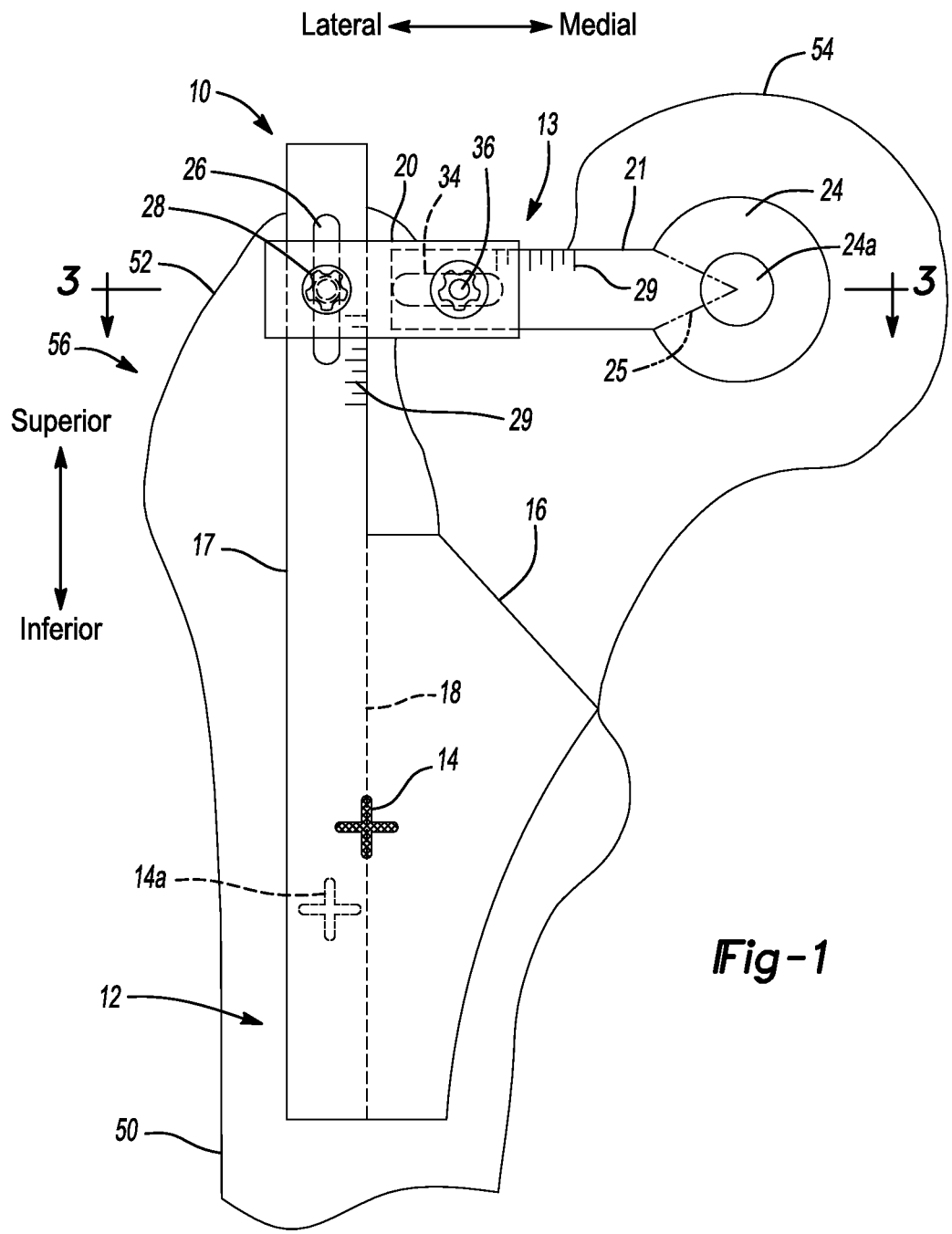
FIG. 1 is a side view of a template positioned adjacent to a femur according to the present teachings.

Example embodiments will now be described more fully with reference to the accompanying drawings.

With initial reference to FIGS. 1-5, a template 10 for locating a native head center of a femur according to the present teachings is illustrated. The template 10 includes a first member 12 and a second member 13. The second member 13 comprises a rectangular plate 20 and a target portion 21. The first member 12 includes a marking feature and optionally a cut guide surface 16. The marking feature can be one or more noncircular marking passages 14 or 14a or the marking feature can be a marking protrusion (FIG. 6, at reference numeral 76). When the cut guide 16 is present, the marking passage 14 can be located further from an edge 17 opposite the cut guide 16 than if the cut guide 16 was not present. When the cut guide 16 is not present, the first member 12 has an edge 18 and the marking passage 14a can be located closer to the opposite edge 17 and the first member 12 may be narrower than when the cut guide 16 is included. It will be understood that the marking passage 14, 14a or marking protrusion (FIG. 6, at reference numeral 76) can be placed at any appropriate location on the template 10 to allow marking of the femur. Further, the marking passage 14, 14a can be any appropriate non-circular shape to allow the template 10 to be properly reoriented when placed over the mark and the mark is viewed through the passage 14, 14a (e.g. the mark can be viewed completely through the marking passage). Thus, the passage 14, 14a may be square, triangular, trapezoidal, etc.

The target portion 21 can terminate with a flat surface, such as a targeting disc 24, with a centric viewing hole 24a or alternatively the target portion 21 can terminate in a targeting point 25. The plate 20 of the second member 13 is operably fixed relative to the first member 12 by a first set screw 28 that passes through a first hole 30 in the plate 20 and through a first slot 26 formed in the first member 12 and is secured by a first nut 32. This configuration allows for the second member 13 to slide along the first member 12 which can be superior to inferior of a patient. Tightening the first set screw 28 through the first nut 32 fixes the second member 13 in a desired position relative to the first member 12.

Figure 2:
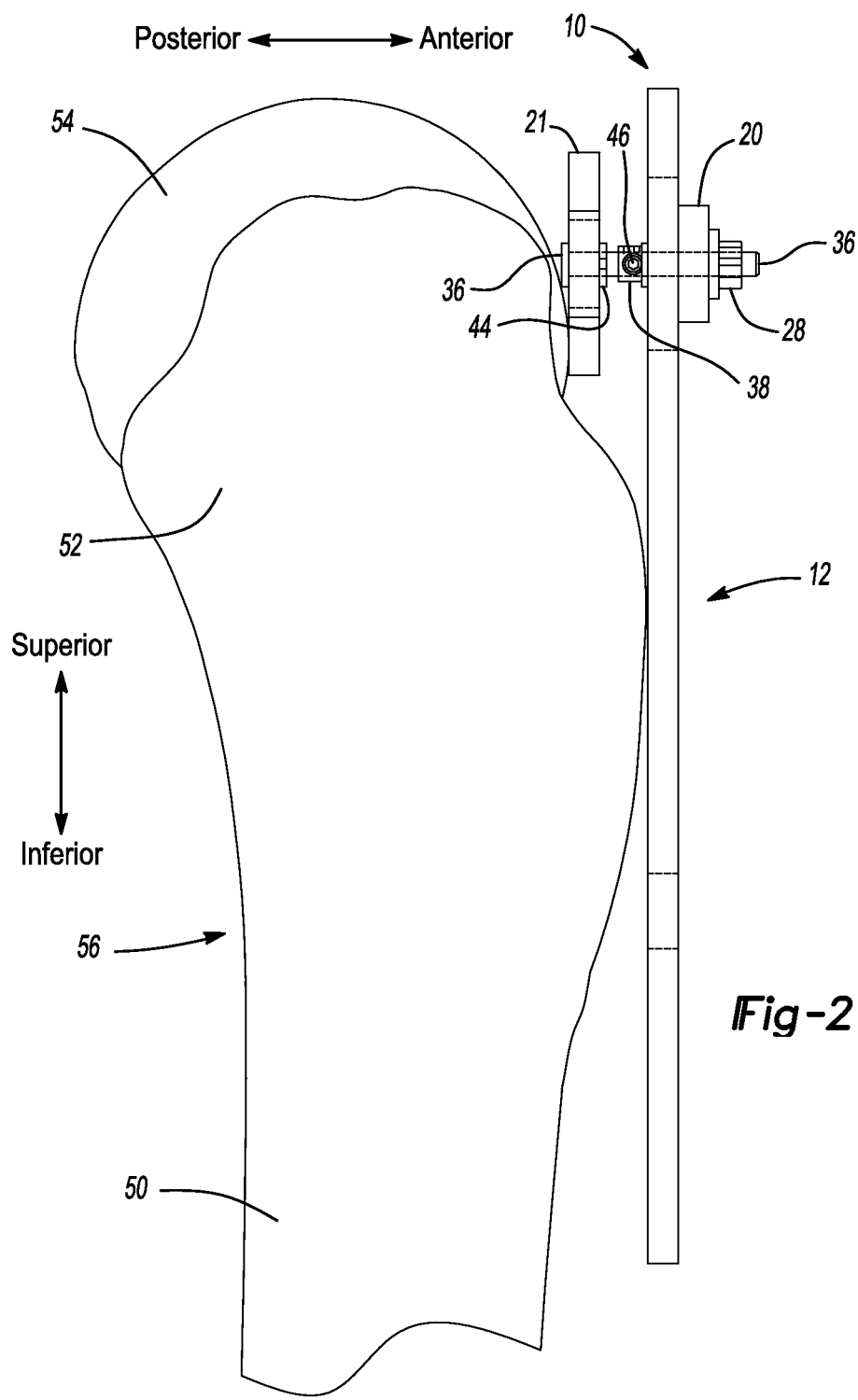
FIG. 2 is a perspective view of the template and femur of FIG. 1.
Figure 3:
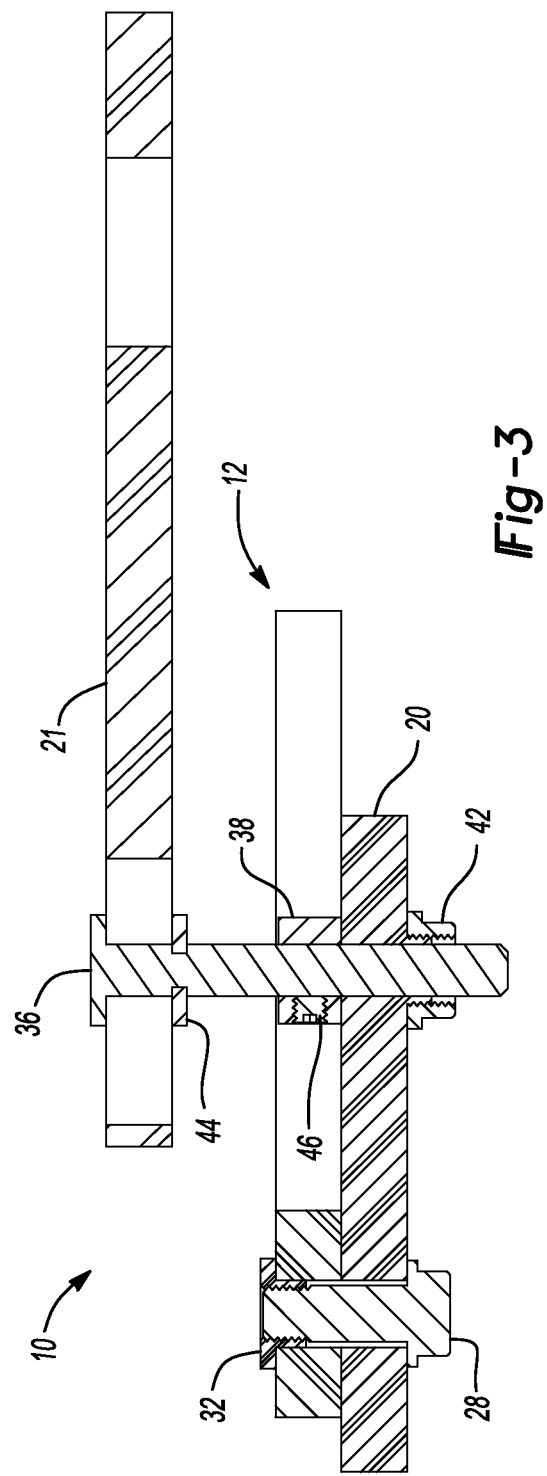
FIG. 3 is a perspective view of the template of FIG. 1.
Figure 4:
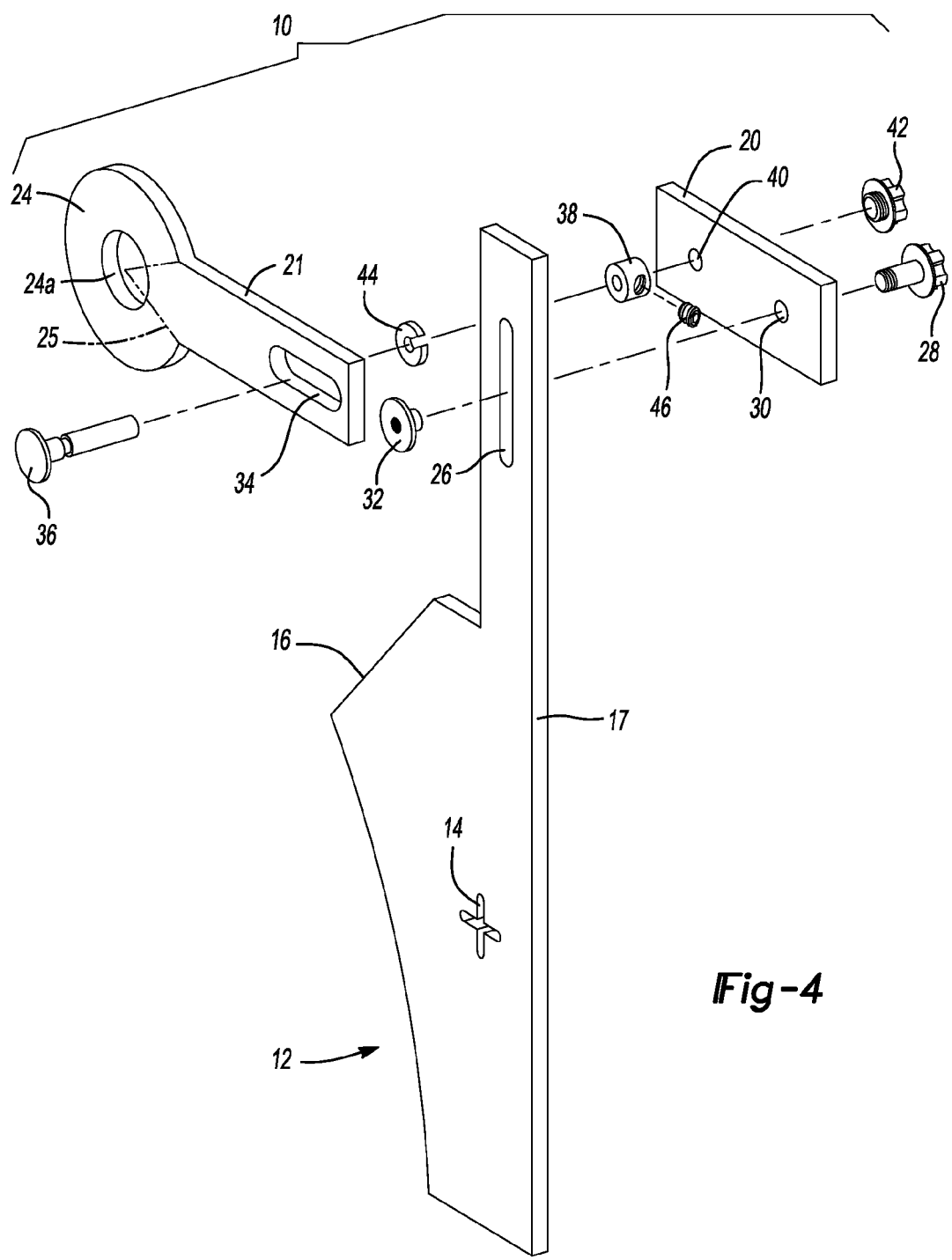
FIG. 4 is an exploded view of the template according to FIG. 1.

Additionally, the plate 20 is operably fixed to the target portion 21 by a second set screw 36 that passes through a second slot 34 formed in target portion 21 and collar 38 permanently connected to the plate 20 through a second hole 40 and secured by a second nut 42. This configuration allows for the target portion 21 to slide in the posterior and anterior directions relative to a patient. Placing a C-clip 44 (FIG. 2) on second set screw 36 on the medial face of the plate 20 fixes the target portion 21 in a desired position relative to the first member 12. Furthermore, the second set screw 36 is operable to allow sliding of the target portion 21 in medial and lateral directions relative to a patient. As depicted in FIG. 2, a screw 46 can be tightened to fix the second set screw 36 and target portion 21 in a desired position relative to the first member 12.

The present teachings additionally provide a method for locating a center of rotation of a native head of a femur and reestablishing the center of rotation with an implanted prosthesis. With further reference to FIGS. 1 and 2, the template 10 described above is inserted through a surgical opening and positioned on an anterior surface of a shaft 50 of a femur 56, on a greater trochanter 52 of the femur 56, or both. If a wide template, such as where the cut guide 16 is present, is used, the shaft 50 of the femur 56 can be marked through the marking passage 14 in the template 10 by means commonly used in the art, such as for example, by drawing, etching, scribing, burning, etc. The marking can be performed, for example, with a marker or an electrosurgical device, such as those sold by Bovie Medical Corporation. If the cut guide 16 is not present, then the shaft 50 of the femur 56 can be marked through the marking passage 14*a* of the template 10 by the same means described above. Alternatively, template 10 can include a marking protrusion (FIG. 6, at reference numeral 76) around which a mark 93 can be drawn, etched, scribed, burned, etc. The second member 13 of the template 10 can be moved relative to the first member 12 to align the target portion 21 with the native head center 54 of the femur 56. The movement can be done to assess or determine version of the anatomy and determine the native head center 54 of the femur 56. The target portion 21 of the second member 13 can be moved in the medial-lateral and anterior-posterior directions along the second set screw 36. A physician can look through the centric hole 89, 24*a* to see better the native head center 54 of the femur 56. The target portion 21 can be fixed in the medial-lateral direction by tightening screw 46 and in the anterior-posterior direction by inserting the C-clip 44 on the second set screw 36. When the centric hole 24*a* of the target portion 21 is aligned with the native head center 54 of the femur 56, the set screws can be used to fix the target 24 relative to the first member 12. As an alternative to fixing the target 24 relative to the first member 12, measurement markings 29 on the template 10 can be used to reestablish the position of the target portion 21 relative to the first member 12 at a later time. The markings can be recorded and reacquired to reset the template 10 to the selected position. Also, the markings can be used to select components of a modular implant system, such as an implant comprising a femur component, a neck component, and a head component, to achieve the measured version and/or reestablish the head center with a prosthesis.

Thus, the target portion 21 can be moved anteriorly, posteriorly, superiorly, inferiorly, medially, and laterally relative to the patient. When the template 10 includes the optional cut guide 16, a line can be drawn along the cut guide 16 for resection. Also, the first member 12 can be fixed to the shaft 50 to act as a guide for resection. Further, when the second member 13 of the template 10 is fixed in all the orientations or the measurement markings 29 have been noted to reestablish the position of the target 24 relative to the first member 12 at a later time, the template 10 can be removed through the surgical opening.

Figure 5:
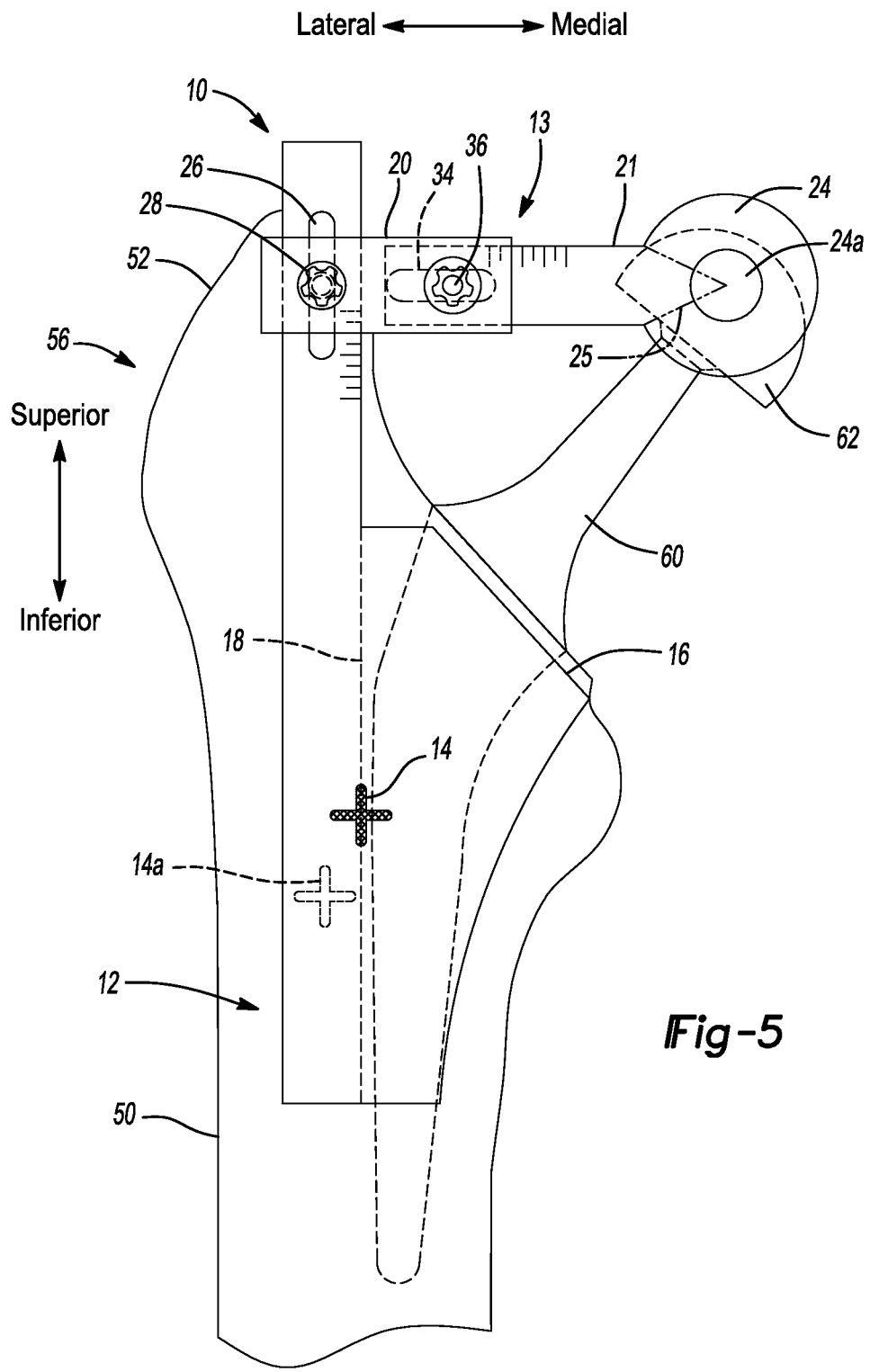
FIG. 5 is a side view of the template according to FIG. 1 positioned adjacent to a femur with an implanted prosthesis.
Figure 6:
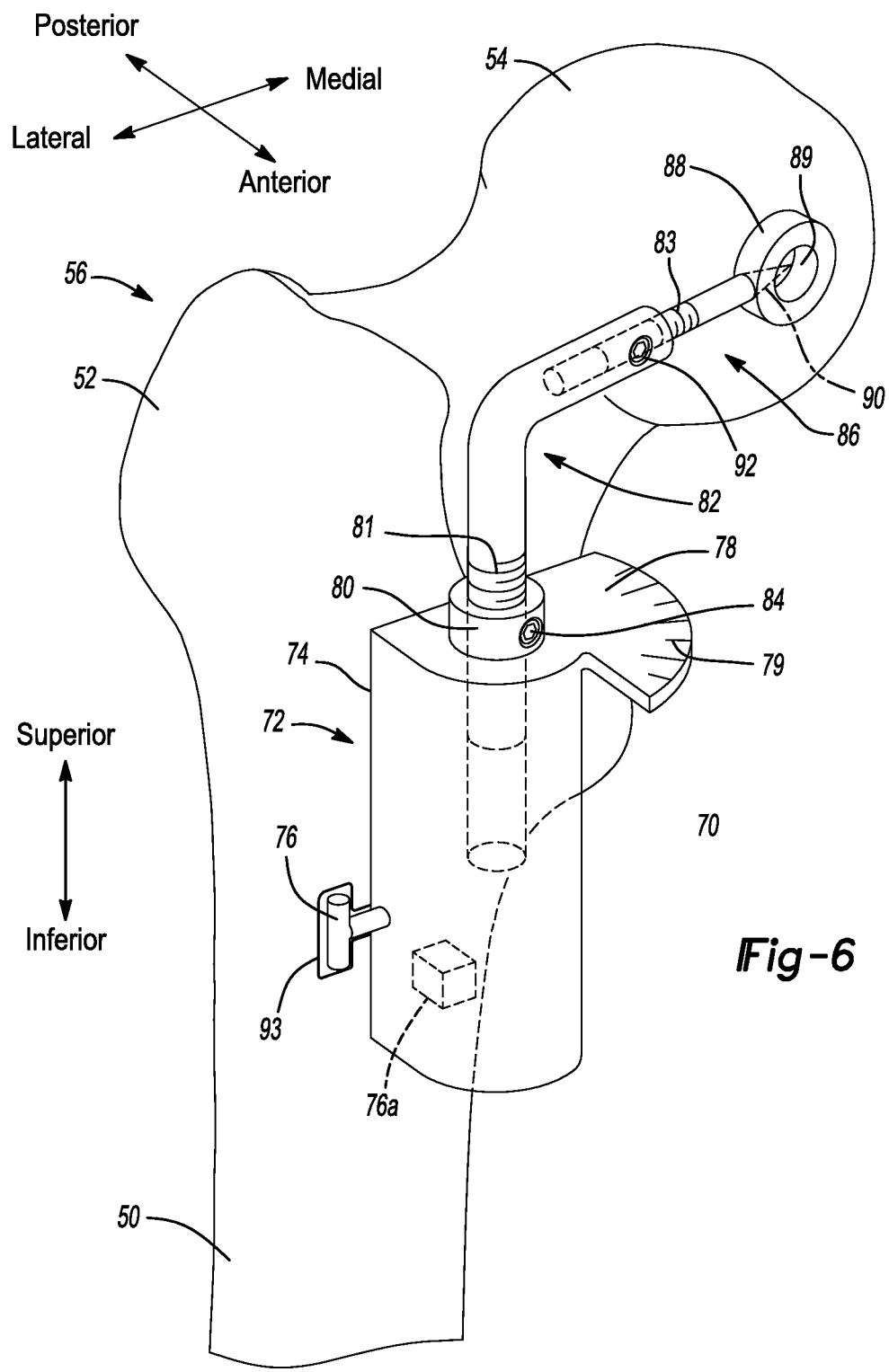
FIG. 6 is a view of a device positioned adjacent to a femur according to the present teachings.

With reference to FIG. 5, the prosthesis 60 can then be inserted into the shaft 50 of the femur. The template 10 can be reinserted through the surgical opening and repositioned on the shaft 50 of the femur and/or on the greater trochanter 52 of the femur. The template 10 can be repositioned in substantially the exact same position on the femur shaft by aligning the mark previously marked on the femur with the marking passage 14, 14*a* or marking protrusion (FIG. 6, at reference numeral 76). The mark is precisely made when first determining the head center and before first removing the template 10. "Substantially the exact same position" is understood to relate to the same location on the femur 56 where the template 10 was positioned for initial head center determination before it was removed, but with consideration for human error which may result in the template 10 being shifted a distance, such as about 1 to about 5 millimeters, in any direction. The targeting disc 24 and viewing hole 24*a*, or alternatively the targeting point 25, of the template 10 is then in substantially the same location as determined to be the center of rotation of the native femoral head 54. The prosthesis 60 can then be manipulated so the center of the prosthesis' head 62 is aligned with the centric viewing hole 24*a* or the targeting point 25 on the target portion 21 of the template 10. For example, the target portion 21 can contact the prosthesis' head 62 at the hole 24*a* or at the tip of the targeting point 25. The implanted prosthesis 60 can then be fixed within the shaft 50 of the femur 56 so the center of rotation of the native head center 54 of the femur 56 is reestablished with the prosthesis' head 62 of the implanted prosthesis 60 when implanted.

The present teachings provide further embodiments for a device 70 for locating a center of rotation of a head center of a femur including a template illustrated in FIG. 6. The device 70 includes a first member 72 that has a flat face 74 to come in contact with the shaft 50 or with a greater trochanter 52 of the femur 56. The first member 72 includes a marking feature, such as a marking protrusion 76 or marking passage 76*a*, for marking a position of the device 70 on the shaft 50 of the femur 56 or on the greater trochanter 52. Optionally, the first member 72 can include an angular measurement device, such as a protractor 78. The protractor 78 can include demarcations 79 for measuring an angle relative to the first member 72, such as the flat face 74 contacting the shaft 50.

A second member 82 of the device 70 slides into the first member 72 through a collar 80 that is connected to the first member 72. The second member 82 is operable to slide in superior to inferior directions and rotate in anterior to posterior directions. A first set screw 84 can be tightened to fix the second member 82 in a selected position relative to the first member 72.

A third member 86 of the device 70 slides into the second member 82 and can move in a medial to lateral direction. The second member includes a target 88 with a centric viewing hole 89, or in the alternative, a targeting point 90. A second set screw 92 can be tightened to fix the third member 86 in a selected position relative to the first member 72.

The present teachings provide a method for determining a center of rotation of a native femoral head and reestablishing the center of rotation with the head 62 of an implanted prosthesis, as illustrated in FIG. 5, with the device 70 represented in FIG. 6. Referring once again to FIG. 6, the device 70 can be inserted through a surgical opening and placed on the femoral shaft 50 and/or greater trochanter 52. The femur 56 can be marked with a mark 93 around the marking protrusion 76 of the first member 72. The second member 82 can be moved in the superior-inferior and anterior-posterior directions to put the target 88 and/or viewing hole 89, or alternatively the targeting point 90, in position to be aligned with the head center 54 of the femur 56. The first set screw 84 can be tightened to fix the second member 82 in place relative to the first member 72. The third portion 86 can also slide in the medial-lateral directions to align the target 88 and/or viewing hole 89, or alternatively the targeting point 90, with the native head center 54 of the femur 56. The position of the third member 86 can be fixed relative to the first member 72 by tightening the second set screw 92.

Alternatively to fixing the second member 82 to the first member 72 and the third member 86 to the second member 82, measurement markings on the second member 82 and on the third member 83 can be used along with the angular measurement device 78 to reestablish the position of the third member 86 relative to the first member 72 at a later time. The centric viewing hole 89 or targeting point 90 can be aligned with the head center. The markings can then be recorded for determining implant components and position during implantation. The recorded markings can also be used to recreate the position of the target positions 89, 90 relative to a positioned prosthesis.

The device 70 can then be removed through the surgical opening so that the native head center 54 of the femur 56 can be resected, as discussed above. When positioning and/or aligning the prosthesis, the device 70 can be positioned in substantially the exact same position where it was when the native head center was being determined with the second and third members 72 and 82 by aligning the mark 93 previously marked on the femur 56 with the marking protrusion 76 of the first member 72 of the device 70. In the embodiment that the members are fixed, the target 88 and/or viewing hole 89, or alternatively the targeting point 90, is then in the same location as the native head center 54 of the femur 56. Alternatively, once the marking protrusion 76 and mark 93 are aligned the measurements can be used to move the members 82 and 86 to reestablish the head center of the prosthesis. A head of an implanted prosthesis can then be manipulated so the center of the head 62 of the prosthesis 60 becomes and remains aligned, such as in contact, with the target 88 of the device 70. The implanted prosthesis 60 can then be fixed within the shaft of the femur 50 so the center of rotation of the native femoral head 54 is reestablished in the head of the implanted prosthesis. Thus, the templates 10, 70 can be used to easier identify version of a prosthesis in a patient.

The present teachings provide various embodiments for a device for locating a center of rotation of a head center of a femur including a template device 100 illustrated in FIGS. 7-9. The device 100 has a first member 102 that may be substantially cylindrical and may be threaded. The first member may have a pointed inferior end 104 to aid in inserting the first member 102 into a shaft 50 of a femur 56 along a central axis 106.

A second member 108 of the template 100 extends from the first member 102. The second member 108 is moveable and fixable relative to the first member 102. The second member 108 includes a first target 110. The first target 110 may include at least one of a centric viewing hole 112 a first targeting point 114. The second member 108 is operable to slide in superior to inferior and lateral to medial directions and rotate in anterior to posterior directions, and vice versa. The second member 108 can be used to identify a first center perspective of a femoral head 54.

A third member 116 of the template 100 extends from the first member 102. The third member 116 is moveable and fixable relative to the first member 102. The third member 116 includes a second target 118. The second target 118 may include at least one of a centric viewing hole 120, or in the alternative, a second targeting point 122. The third member 116 is operable to slide in superior to inferior and lateral to medial directions and rotate in anterior to posterior directions, and vice versa. The third member 16 can be used to identify a second center perspective of a femoral head 54.

Additionally, the present teachings provide a method for determining a native head center of a femur and reestablishing the native head center of the femur with a head of an implanted prosthesis by use of template 100 represented in FIGS. 7-9. The method comprises positioning at least a portion the first member 102 of the template 100 into the shaft 50 of the femur 56 along the central axis 106 of the femur 56. In some instances, it may be necessary to drill a pilot hole into the shaft 50 of the femur 56 along the central axis 106. The first member 102 can be pounded into the shaft 50 of the femur 56, or alternatively, it can be screwed into the shaft 50 if it is threaded. When the first member 102 has been pounded into place, the femur 56 and the first member 102 can be marked at a first position 107 to mark a depth 109.

As shown in FIGS. 7 and 8, when the first member 102 of the template 100 is inserted into the shaft 50 of the femur 56 along the central axis 106, i.e. centered in a superior perspective and in an anterior/posterior perspective, the second member 108 may be moved in the inferior to superior and medial to lateral directions, and in the anterior to posterior direction, or vice versa, to position the first target 118 at a native head center 54 of the femur 56 in a first perspective. The target 110 can be placed at the native head center 54, such as by use of the centric viewing hole 112 or first targeting point 114. Additionally, the third member 116 can move in the inferior to superior, medial to lateral directions, and the anterior to posterior direction, or vice versa, to position the second target 118 at the native head center 54 of the femur 56 in a second perspective, such as by use of the centric viewing hole 120 or second targeting point 122.

When the second member 108 and the third member 116 have been oriented in order to position the targets 110 and 118 at the native head center 54 of the femur 56, the second and third members 108, 116 can be fixed relative to the first member 102. A locking member can be tightened to fix the second member 108 in the selected position relative to the first member 102. The locking member can be tightened to fix the third member 116 in the selected position relative to the first member 102. Alternatively, separate locking members can be present to fix the second member 108 and third member 116 in selected positions. The femur 56 and the first, second or third member 102, 108, 116 can be marked at a second position 121. The template 100 can then be removed from the shaft 50 of the femur 56, and the native femoral head can be removed.

With reference to FIG. 9, when the native femoral head has been removed, a broach or prosthesis 124 can be inserted into the shaft 50 of the femur 56. The broach or prosthesis 124 may engage at least a first portion of the first member 102, such as with a bore capable of accepting the first member 102 of the template 100. The hole of the broach or prosthesis 124 is aligned along the central axis 106 of the shaft 50 of the femur 56. Aligning the mark at the first position 107 on the femur 56 and the first member 102 ensures the broach or prosthesis 124 has been inserted to the shaft 50 to the depth 109. When the broach or prosthesis 124 is in place, the native head center 54 of the femur 56 can be reestablished by rotating the first member 102 of the template 100 in the hole defined by the broach or prosthesis 124 until the mark at the second position 121 (as referenced in FIG. 8) has been aligned between the femur 56 and the first, second or third member 102, 108, 116.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for determining a native head center of a femur and reestablishing the native head center of the femur with a head of an implanted prosthesis comprising: positioning a template comprising a first member that is both operably connected to and movable relative to a second member on an surface of a femur, wherein the femur has a shaft and a native head with a center of rotation, wherein the second member includes a target portion configured to be positioned to identify a center of the native femoral head; marking the position of the template on the femur by placing a mark on the femur using a marking feature associated with the first member of the template; centering the target portion of the second member near the native head center of the femur by moving the second member relative to the first member; removing the template and resecting the native head of the femur, wherein the native head center of the femur can be reestablished by positioning the template on the marked surface of the femur and aligning the mark on the femur with the marking feature associated with the first member of the template; and guiding a resection of the native femoral head with a cut guide defined by the template.

2. The method according to claim 1, further comprising: making a surgical opening in a patient;
   placing the template through the surgical opening; and
   positioning the template on the femur.

3. The method according to claim 1, further comprising:
   tightening locking members to fix the second member in a selected position relative to the first member.

4. The method according to claim 1, wherein the template further comprises a third member operably connected to and fixable to the second member.

5. The method according to claim 1, further comprising fixing the second member in a position relative to the first member by a first locking member; and
   fixing the third member in a position relative to the first member by a second locking member.

6. The method according to claim 1, further comprising:
   determining a position measurement of the second member in a selected position relative to the first member with measurement markings; and
   selecting a prosthesis based on the position measurement.

* * * * *